(12) United States Patent
Keller et al.

(10) Patent No.: US 12,345,957 B2
(45) Date of Patent: Jul. 1, 2025

(54) POSITION VARIATIONS OF THE LENSES OF AN EYEWEAR EQUIPMENT

(71) Applicant: ESSILOR INTERNATIONAL, Charenton-le-Pont (FR)

(72) Inventors: Gerhard Keller, Charenton-le-Pont (FR); Aurélie Le Cain, Charenton-le-Pont (FR); Konogan Baranton, Charenton-le-Pont (FR); Sébastien Fricker, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 530 days.

(21) Appl. No.: 17/780,847

(22) PCT Filed: Jan. 4, 2021

(86) PCT No.: PCT/EP2021/050023
§ 371 (c)(1),
(2) Date: May 27, 2022

(87) PCT Pub. No.: WO2021/140070
PCT Pub. Date: Jul. 15, 2021

(65) Prior Publication Data
US 2023/0017742 A1    Jan. 19, 2023

(30) Foreign Application Priority Data
Jan. 10, 2020   (EP) .................................. 20305014

(51) Int. Cl.
*A61B 5/11*    (2006.01)
*G02C 13/00*   (2006.01)

(52) U.S. Cl.
CPC .......... *G02C 13/005* (2013.01); *A61B 5/1114* (2013.01)

(58) Field of Classification Search
CPC ........................... G02C 13/005; A61B 5/1114
(Continued)

(56) References Cited

U.S. PATENT DOCUMENTS 10,108,847 B2 * 10/2018 Arikawa .............. G06V 20/653
10,216,011 B2 *  2/2019 Pfeiffer ................ G02C 13/005
(Continued)

FOREIGN PATENT DOCUMENTS

| CN | 102498430 A | 6/2012 |
|---|---|---|
| CN | 105319718 A | 2/2016 |

(Continued)

OTHER PUBLICATIONS

International Search Report and Written Opinion of the ISA for PCT/EP2021/050023, mailed Mar. 31, 2021, 14 pages.
(Continued)

*Primary Examiner* — George B Bennett
(74) *Attorney, Agent, or Firm* — NIXON & VANDERHYE (57) ABSTRACT

A method for determining a position variation of an eyewear equipment worn by a wearer includes obtaining reference data representing a reference position of an eyewear equipment worn by the wearer, the eyewear equipment including at least one ophthalmic lens and a frame on which the at least one ophthalmic lens is mounted, determining at least one reference position parameter indicative of a reference position of the eyewear equipment on the face of the wearer based on the reference data, obtaining current data representing a current position of the eyewear equipment worn by the wearer, determining at least one current position parameter indicative of a current position of the eyewear equipment in front of the eyes of the wearer based on the current data, and comparing the reference and current positions
(Continued)

parameters to determine a position variation of the eyewear equipment worn by the wearer.

14 Claims, 6 Drawing Sheets

(58) Field of Classification Search
USPC .......................................................... 33/200
See application file for complete search history.

(56) References Cited

U.S. PATENT DOCUMENTS

| | | | |
|---|---|---|---|
| 10,386,657 B2* | 8/2019 | El-Hajal | A61B 3/0025 |
| 11,181,758 B2* | 11/2021 | Briggs | G02C 13/005 |
| 11,488,239 B2* | 11/2022 | Goldberg | G02C 13/005 |
| 11,815,744 B2* | 11/2023 | Le Cain | G06T 7/70 |
| 12,044,902 B2* | 7/2024 | Baranton | G06T 7/73 |
| 12,130,501 B2* | 10/2024 | Quere | G02C 7/027 |
| 2009/0128579 A1* | 5/2009 | Xie | G02C 13/005 |
| | | | 345/634 |
| 2015/0309338 A1 | 10/2015 | Chauveau | |
| 2016/0034032 A1 | 2/2016 | Jeong | |
| 2018/0024384 A1 | 1/2018 | Tadokoro | |
| 2019/0324291 A1 | 10/2019 | Hatanaka | |
| 2019/0331939 A1* | 10/2019 | Martin | G02C 13/005 |
| 2020/0218095 A1 | 7/2020 | Gamperling et al. | |

FOREIGN PATENT DOCUMENTS

| | | |
|---|---|---|
| CN | 105573627 A | 5/2016 |
| CN | 106461969 A | 2/2017 |
| DE | 10 2004 063160 | 7/2006 |
| DE | 10 2008 018198 | 10/2009 |
| EP | 3 226 068 | 10/2017 |
| EP | 3267239 A1 | 1/2018 |
| EP | 3 422 087 | 1/2019 |
| EP | 3 561 577 | 10/2019 |
| WO | 2008/009355 | 1/2008 |
| WO | 2015147758 A1 | 10/2015 |
| WO | 2016/156600 | 10/2016 |
| WO | 2018/124311 | 7/2018 |

OTHER PUBLICATIONS

Oswald et al., "Visioffice and eyecode: Die Messung f?r perfektes Sehen-Teil 1 Visioffice", Deutsche Optiker Zeitung Doz, No. 5-2009, Jan. 1, 2009, pp. 46-50.

Oswald et al., "Visioffice und eyecode: Die Messung f?r perfektes Sehen Tei 12: eyecode", Deutsche Optiker Zeitung Doz, No. 10/2009, Jan. 1, 2009, pp. 38-43.

"Impressionist—Das 4-in-1 Integrierte Service-Terminal Von Rodenstock", Deutsche Optiker Zeitung, Jan. 1, 2006, pp. 56-61.

Office Action, issued in Chinese Patent Application No. 202180006464.1 dated Dec. 29, 2023.

* cited by examiner

POSITION VARIATIONS OF THE LENSES OF AN EYEWEAR EQUIPMENT

This application is the U.S. national phase of International Application No. PCT/EP2021/050023 filed Jan. 4, 2021 which designated the U.S. and claims priority to EP 20305014.1 filed Jan. 10, 2020, the entire contents of each of which are hereby incorporated by reference.

TECHNICAL FIELD

The disclosure relates to the correct fitting of an eyewear equipment on the face of the wearer. In particular, the disclosure relates to a method for determining a position variation of an eyewear equipment worn by a wearer. The disclosure also relates to a method for selecting the most adapted lens for a wearer and to a method for adjusting an electro-active function of an active lens.

Furthermore, the disclosure relates to a computer program product comprising one of more stored sequences of instruction that is accessible to a processor.

BACKGROUND

Conventionally, when a person purchases an eyewear equipment, an optician performs an adjustment of the frame directly on the face of the wearer, manually, depending on indications of comfort that the wearer provides him with and know-how gained from experience.

When the wearer carries various activities while he is wearing the eyewear equipment, the position of the eyewear equipment on the face of the wearer tend to vary. Due to gliding, sliding and frame deformation, the lenses may no longer be properly aligned in front of the eyes of the wearer, and thus the visual comfort of the wearer may decrease.

In WO 2016/156600 A1 the position of a head-mounted device is tracked using sensors. However, such method requires a specific head-mounted device and thereby is not applicable to any kind of eyewear equipment.

Therefore, there is a need for a simple solution to quickly and accurately measure and determine how any eyewear equipment shift on the face of a wearer

SUMMARY

To this end, the disclosure proposes a method for determining a position variation of an eyewear equipment worn by a wearer, the method comprising:
  obtaining reference data representing a reference position of an eyewear equipment worn by the wearer, the eyewear equipment comprising at least one ophthalmic lens and a frame on which the at least one ophthalmic lens is or will be mounted;
  determining at least one reference position parameter indicative of a reference position of the eyewear equipment in front of the eyes of the wearer based on the reference data;
  obtaining current data representing a current position of the eyewear equipment worn by the wearer;
  determining at least one current position parameter indicative of a current position of the eyewear equipment in front of the eyes of the wearer based on the current data;
  comparing the reference and current positions parameters so as to determine a position variation of the eyewear equipment worn by the wearer.

Advantageously, the method according to the disclosure allows to easily and accurately determine and quantify the variation of position of an eyewear equipment worn by a wearer.

According to further embodiments which can be considered alone or in combination:
  the steps of obtaining current data, determining a current position parameter, and the step of comparing the reference and current position parameters are repeated over time so as to evaluate the position variations of the eyewear equipment over time; and/or
  the method further comprises obtaining a threshold value corresponding to a level of discomfort, the level of discomfort being indicative of an index of visual performance of the wearer wearing the eyewear equipment in the current position; and/or
  the method further comprises comparing the threshold value and the position variation of the eyewear equipment worn by the wearer; and/or
  the method further comprises sending a notification to the wearer and/or an eye-care professional when the position variation of the eyewear equipment worn by the wearer is higher than the threshold value; and/or
  the method further comprises obtaining lens data relating to a prescription of a wearer and/or the design of the at least one lens of the eyewear equipment; and/or
  the method further comprises determining a threshold value corresponding to a level of discomfort of the wearer based on the lens data and the position variation of the eyewear equipment; and/or
  the index of visual performance relates to an acuity loss and/or an accommodation effort and/or a resulting astigmatism and/or a vergence effort and/or a diplopia; and/or
  the method further comprises obtaining sensitivity data indicative of the sensitivity of the wearer to optical aberrations; and/or
  the threshold value is determined based on the lens data, the position variation of the eyewear equipment and the sensitivity data; and/or
  the position of the eyewear equipment corresponds to the position of the two lenses of the eyewear equipment worn by the wearer, for example the position of the two lenses in front of each respective eye of the wearer; and/or
  the reference and current data comprises at least one picture of the face of the wearer wearing the eyewear equipment; and/or
  the reference and current data comprises a 3D scan of the face of the wearer wearing the eyewear equipment; and/or
  the reference and current position parameter corresponds to pupil position in a boxing reference frame for primary gaze posture, and/or position of at least one eyewear feature relative to at least one face feature, and/or vertex distance, and/or pantoscopic angle of the lens according to the primary gaze posture, and/or wrap angle of the lens, and/or lens rotation angle, and/or pupil relative to the lens fitting cross; and/or
  the current data are obtained after at least a minimal wearing time; and/or
  the minimal wearing time is two weeks.

The disclosure further relates to a method for selecting the most adapted eyewear equipment for a wearer, the method comprising
  providing multiple eyewear equipment;

determining a position variation of the eyewear equipment worn by the wearer for each eyewear equipment according to the method of the disclosure;

comparing the position variation of each eyewear equipment; and selecting the eyewear equipment having the smallest position variation.

Advantageously, the method according to the disclosure allows providing to a wearer an eyewear equipment that is best adapted for him.

The disclosure further relates to a method for adjusting an optical function of an electro-active eyewear equipment worn by a wearer, the method comprising:

determining a position variation of the electro-active equipment according to the method of the disclosure;

obtaining prescription data indicative of a prescription of the wearer; and adjusting the optical function of the active lens based on the position variation and the prescription data.

Advantageously, adjusting the optical function of the active lens according to the method of the disclosure allows compensating the movement of the eyewear equipment worn by the wearer to provide the best and most adapted optical function.

The disclosure further relates to a computer-readable storage medium having a program recorded thereon, wherein the program makes the computer execute a method according to the disclosure.

BRIEF DESCRIPTION OF THE DRAWINGS

Embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help to improve the understanding of the embodiments of the present invention.

DETAILED DESCRIPTION

The disclosure relates to a method, for example implemented by computer means, for determining a position variation of an eyewear equipment worn by a wearer.

In the context of the invention, the term "eyewear equipment" may refer to a head-mounted device such as for example spectacles. The eyewear equipment comprises at least one optical lens, for example an ophthalmic lens and a frame on which the at least one optical lens is mounted. The eyewear equipment is adapted to a person and to be worn in front of the eyes of said person.

Figure 1:
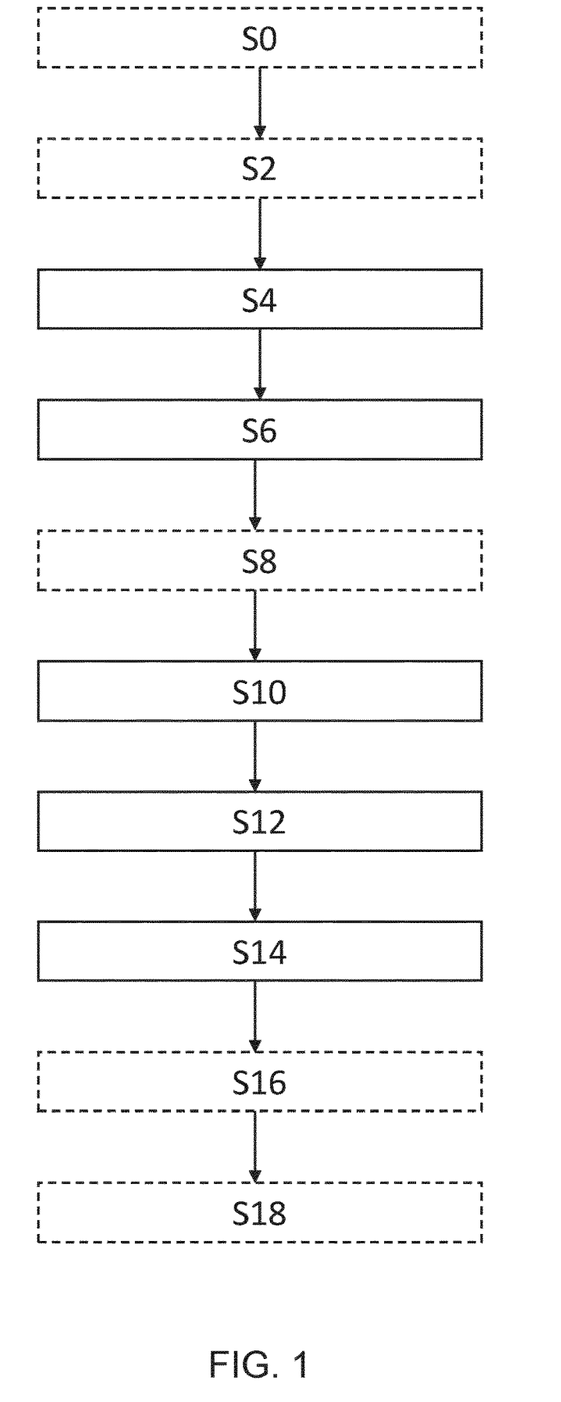
FIG. 1 illustrates a chart-flow embodiment of the method for determining a position variation of an eyewear equipment worn by a wearer.

As illustrated on FIG. 1, the method for determining a position variation of an eyewear equipment worn by a wearer comprises a step S4 of obtaining reference data.

The reference data represent a reference position of the eyewear equipment worn by the wearer. Typically, after the wearer selected an eyewear equipment, the eye care professional adjusts the frame of the eyewear equipment to have it perfectly fit the face of the wearer. In particular, the eye care professional adjusts the frame of the eyewear to perfectly position the at least one optical lens in front of the eyes of the wearer. For example, the position of the eyewear equipment refers to the position of two lenses of the eyewear equipment in front of each respective eye of the wearer wearing said eyewear equipment. Such position of the eyewear equipment corresponds to the reference position. Once the eyewear equipment is placed on the face of the wearer in the reference position, reference data are acquired.

According to an embodiment of the disclosure, the reference data comprise at least one picture of the face of the wearer wearing the eyewear equipment in a reference position. For example, the eye care professional may take at least one reference picture, for example using a Visioffice®, of the face of the wearer on which the eyewear equipment is positioned.

According to another embodiment of the disclosure, the reference data comprise at least one three dimensional scan of the face of the wearer wearing the eyewear equipment in the reference position. Advantageously, acquiring three dimensional measurement of the face of the wearer wearing the eyewear equipment in the reference position allows identifying with more precision the position and the orientation of the eyewear equipment with respect to the face of the wearer.

The method for determining a position variation of an eyewear equipment worn by a wearer further comprises a step S6 of determining a reference position parameter based on the reference data. The reference position parameter is indicative of the reference position of the eyewear equipment on the face of the wearer.

According to an embodiment of the disclosure, the reference position parameter corresponds to the position of at least one eyewear equipment feature relative to at least one face feature. The face feature refers to any structure of the face of the wearer such as for example the nose, the eyebrows, the cheeks, the ears the eyes' corners etc. The eyewear equipment feature refers to any identifiable structure of the eyewear equipment such as the bottom edge of the lenses, the top edge of the lenses, the bridge, the shape or contour of the lenses, the temples of the frame etc.

Figure 2A:
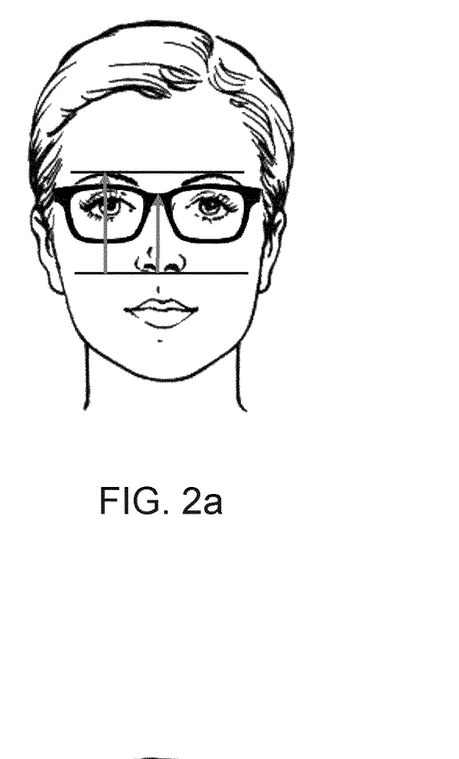
FIGS. 2a and 2b illustrate a variation position of an eyewear equipment.

As illustrated on FIG. 2a, using the reference data, it is possible to determine the position of a fixed structure, i.e. the face feature, the position of a structure that is likely to vary, i.e. the eyewear equipment feature, and to compute the relative position of these at least two features to determine a reference parameter. Typically, the distance between at least two face features and the distance between one of these two face features and an eyewear equipment feature are compared to determine the reference parameter. For example, using a picture of the face of the wearer wearing the eyewear equipment in the reference position, it is possible to determine the position of the eyebrows and the position of the base of the nose of the wearer. Similarly, using a picture of the face of the wearer wearing the eyewear equipment in the reference position, it is possible to determine the position of the bridge of the eyewear equipment. By comparing the distance between the base of the nose and the eyebrows of the wearer and the distance between the base of the nose and the bridge of the eyewear equipment, it possible to determine the relative position of the eyewear feature.

According to another embodiment of the disclosure, the reference position parameter corresponds to a pupil position in a boxing reference frame for a predefined gaze direction and/or head posture, for example the primary gaze posture.

Figure 8:
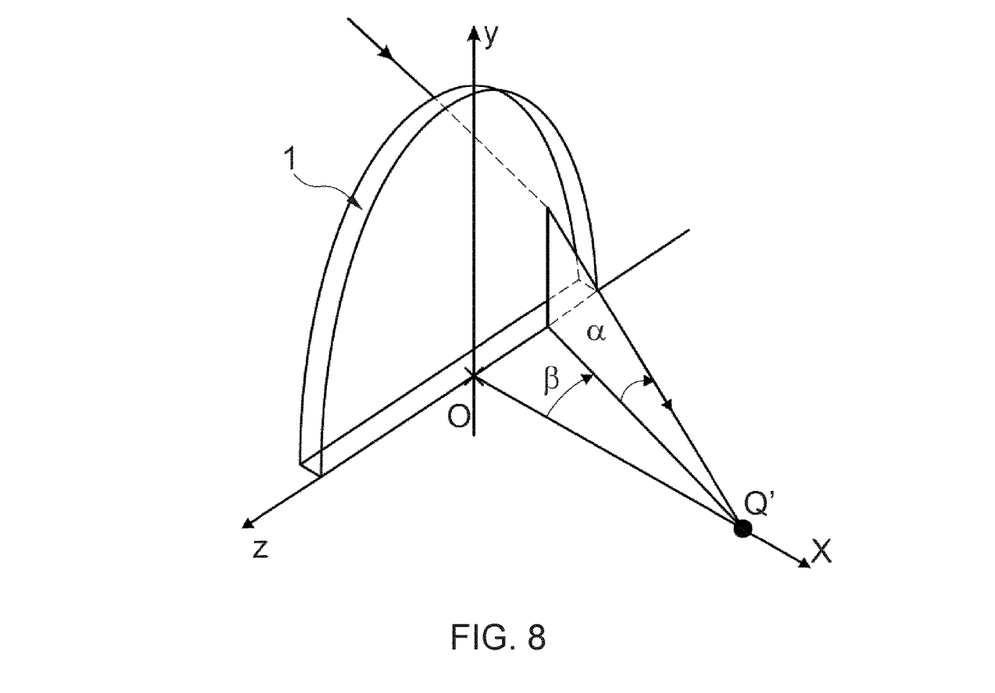
FIGS. 8 and 9 diagrammatically illustrate optical systems of eye and lens.
Figure 9:
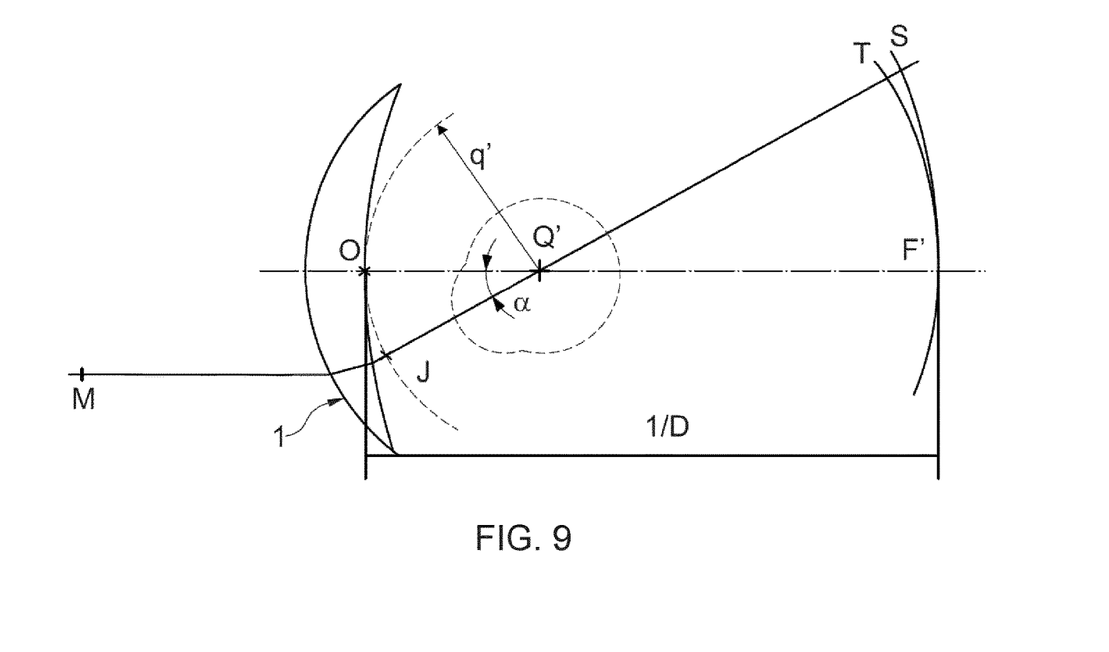

The gaze direction is defined by two angles measured with regard to a direct orthonormal basis centered on the center of rotation of the right or left eye. FIGS. 8 and 9 are diagrammatic illustrations of optical systems of eye and lens, thus showing the definitions used in the description. More precisely, FIG. 8 represents a perspective view of such a system illustrating parameters α and β used to define a gaze direction. FIG. 9 is a view in the vertical plane parallel to the anteroposterior axis of the wearer's head and passing through the center of rotation of the eye in the case when the parameter β is equal to 0.

The center of rotation of the eye is labeled Q'. The axis Q'F', shown on FIG. 9 in a dot-dash line, is the horizontal axis passing through the center of rotation of the eye and extending in front of the wearer—that is the axis Q'F' corresponding to the primary gaze view. This axis cuts the aspherical surface of the lens on a point called the fitting cross, which is present on lenses to enable the positioning of lenses in a frame by an optician. The point of intersection of the rear surface of the lens and the axis Q'F' is the point O. O can be the fitting cross if it is located on the rear surface. An apex sphere, of center Q', and of radius q', is tangential to the rear surface of the lens in a point of the horizontal axis. As examples, a value of radius q' of 25.5 mm corresponds to a usual value and provides satisfying results when wearing 5 the lenses.

A given gaze direction—represented by a solid line on FIG. 8—corresponds to a position of the eye in rotation around Q' and to a point J of the apex sphere; the angle β is the angle formed between the axis Q'F' and the projection of the straight line Q'J on the horizontal plane comprising the axis Q'F'. The angle α is the angle formed between the axis Q'J and the projection of the straight line Q'J on the horizontal plane comprising the axis Q'F'; this angle appears on the scheme on FIGS. 8 and 9. A given gaze view thus corresponds to a point J of the apex sphere or to a couple (α, β). The more the value of the lowering gaze angle is positive, the more the gaze is lowering and the more the value is negative, the more the gaze is rising.

Figure 3A:
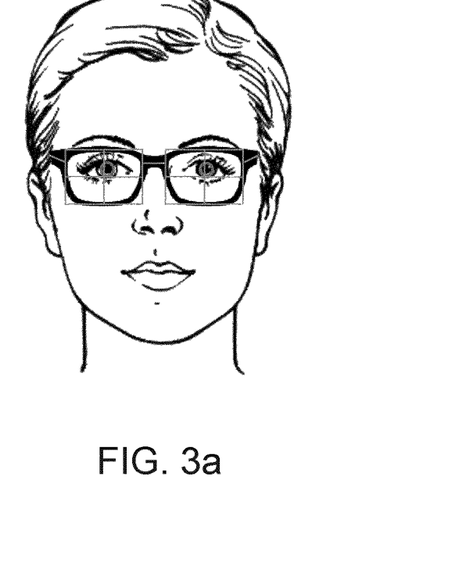
FIGS. 3a and 3b illustrate a variation position of an eyewear equipment.

As illustrated on FIG. 3*a*, using the reference data comprising for example a picture or a 3D scan of the face of the wearer wearing the eyewear equipment in the reference position, it is possible to calculate the head position and the position of the eyewear equipment relatively to the camera, for example using face tracking algorithm. The reference position of the eyewear equipment on the face of the wearer may then be modeled as a boxing reference frame. For each gaze direction, the relative position of the pupil of each eye in their respective boxing reference frame may be used to determine a reference position parameter.

According to another embodiment of the disclosure, the reference position parameter corresponds to a pupil position relative to the fitting cross of the lens of the eyewear equipment. For a gaze direction, the position of the pupil of the eye of the wearer relative to the position of the fitting cross of the lens of the eyewear equipment positioned on the face of the wearer in the reference position may be used to determine a reference position parameter.

According to another embodiment of the disclosure, the reference position parameter corresponds to a vertex distance. The vertex distance is the distance between the back surface of the lens of the eyewear equipment and the apex of the cornea of the respective eye of the wearer, measured usually along the visual axis of the eye in a primary position, usually taken to be the horizontal. Using the reference data, a vertex distance may be used to determine a reference position parameter.

According to another embodiment of the disclosure, the reference position parameter corresponds to a pantoscopic tilt of the lens of the eyewear equipment. The pantoscopic tilt of the lens is defined as the vertical angle about the horizontal axis, with respect to a gaze direction, for example the primary gaze of a wearer. Considering a section of the lens in the (O,y,z) plane defined with reference to FIG. 8, the tangent to this curve at the point O is inclined to the (O,y) axis at an angle called the pantoscopic tilt. For a gaze direction, the pantoscopic tilt of the lens of the eyewear equipment may be used to determine a reference position parameter.

According to another embodiment of the disclosure, the reference position parameter corresponds to a wrap angle of the lens of the eyewear equipment. The wrap angle is defined as the horizontal angle in the vertical plane between the optical axis of the lens of the eyewear equipment and the visual axis of the eye of the wearer for a given gaze direction, for example the primary gaze. Considering a section of the lens in the (O,y,z) plane defined with reference to FIG. 8, the tangent to this curve at the point O is inclined to the (O,x) axis at an angle called the wrap angle. For a gaze direction, the wrap angle of the lens of the eyewear equipment may be used to determine a reference position parameter.

According to another embodiment of the disclosure, the reference position parameter corresponds to a lens rotation angle. Considering a section of the lens in the (O,y,z) plane defined with reference to FIG. 8, the lens rotation angle corresponds to the inclination around the (O,z) axis. For a gaze direction, the lens rotation angle of the lens of the eyewear equipment may be used to determine a reference position parameter.

The method for determining a position variation of an eyewear equipment worn by a wearer further comprises a step S10 of obtaining current data.

The current data represent at least a specific position of the eyewear equipment worn by the wearer at the precise time the data are acquired. Such position of the eyewear equipment is referred as the current position. More precisely, the current data may correspond to the current position of two lenses of the eyewear equipment relative to each respective eye of the wearer wearing said eyewear equipment. The current data may be acquired at any time of the life of the wearer while he is wearing the eyewear equipment. Typically, the current data may be acquired while the wearer is performing an activity, such as for example driving a car, walking, running, reading a book, watching TV etc.

According to an embodiment of the disclosure, the current data comprise at least one picture of the face of the wearer wearing the eyewear equipment in a reference position. For example, pictures of the wearer performing activities while he is wearing the eyewear equipment may be obtained from personal collection or from social media. According to another embodiment of the disclosure, the reference data comprise at least one three dimensional scan of the face of the wearer wearing the eyewear equipment.

The method for determining a position variation of an eyewear equipment worn by a wearer further comprises a step S12 of determining a current parameter based on the current data. The current parameter is indicative of the specific current position of the eyewear equipment on the face of the wearer at the moment the current data are acquired. Preferably, the current data are acquired after a minimal time during which the wearer wears the eyewear equipment. For example, the current data may be acquired after at least one week, preferably two weeks, more preferably one month of wearing the eyewear equipment.

Similarly to the reference position parameter, the current position parameter may correspond to the position of at least one eyewear equipment feature relative to at least one face feature, and/or a pupil position in a boxing reference frame for a predefined gaze direction and/or head posture, and/or a pupil position relative to the fitting cross of the lens of the eyewear equipment, and/or a vertex distance, and/or a pantoscopic tilt of the lens, and/or a wrap angle of the lens, and/or a lens rotation angle.

The method for determining a position variation of an eyewear equipment worn by a wearer further comprises a step 14 of comparing the reference and current position parameters so as to determine a position variation of the eyewear equipment worn by the wearer.

When the reference position parameter and the current position parameter relates at least to the same feature, it is possible to compare them. A difference between these two parameters would reflect a variation from the position of reference of the eyewear equipment worn by the wearer.

Figure 2B:
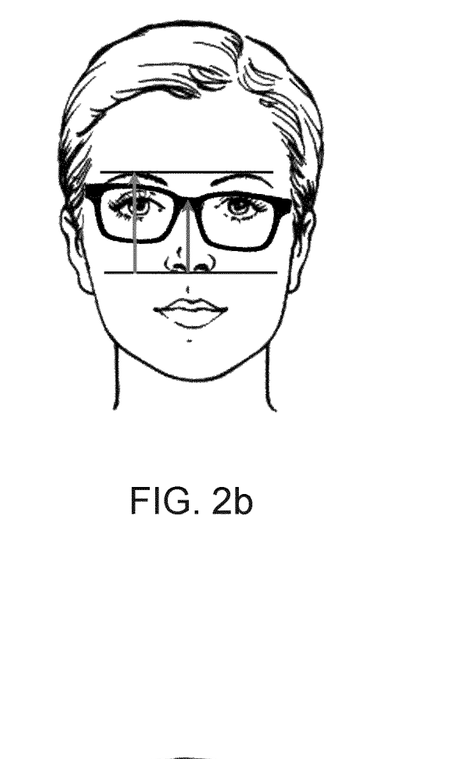

As illustrated on FIG. 2b representing current data, the current position parameter corresponding to the distance between the base of the nose and the bridge of the frame of the eyewear equipment normalized by the distance between the base of the nose and the eyebrows of the wearer is smaller than the reference position parameter corresponding to the distance between the base of the nose and the bridge of the frame of the eyewear equipment normalized by the distance between the base of the nose and the eyebrows of the wearer in FIG. 2a.

Figure 3B:
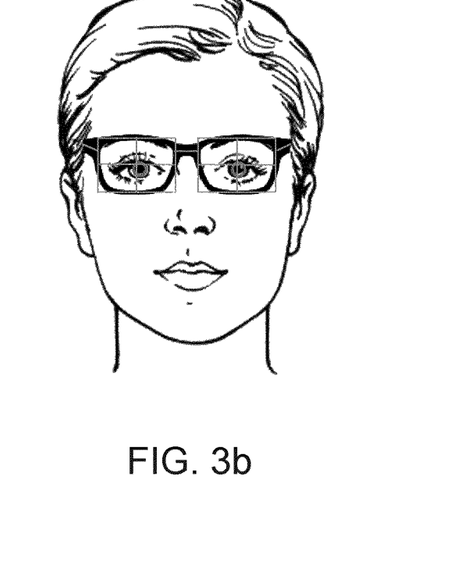

As illustrated on FIG. 3b representing current data, the current position parameter corresponding to the position of the pupils of the wearer in the boxing reference frame differs from the reference position parameter corresponding the position of the pupils of the wearer in the boxing reference frame represented in FIG. 3a. In particular, for a given eye gaze direction with the eyewear equipment in the reference position, the pupil of the eyes of the wearer are positioned in the lower half of the boxing reference frame. On the contrary, for the same given eye gaze direction with the eyewear equipment in the current position, the pupil of the eyes of the wearer are positioned in the upper half of the boxing reference frame.

Advantageously, the method according to the disclosure allows to easily and quickly determine position variation of the eyewear equipment worn by a wearer.

The steps of obtaining current data, determining a current position parameter and comparing the reference and current position data to determine a position variation of the eyewear equipment may be repeated over time so as to evaluate the positions variations of the eyewear equipment over time.

Positions variations may be evaluated once a week. The frequency of the evaluation could be more frequent being every day or every two, three, four, five or six days. The evaluation could also be less frequent, for example, once every two weeks or once a month. The evaluation could be even less frequent.

The frequency of the evaluation may be less frequent if the wearer has already been wearing the eyewear equipment for several months or years.

The frequency of the evaluation can also be based on the fact that a variation of the position of the eyewear equipment with respect to the reference position is above a predetermined threshold value relative to at least one wearer's wearing condition parameter. The predetermined threshold may comprise the eye-lens distance, the pantoscopic angle and other data related to the wearer's wearing conditions parameters values. The wearer may tolerate variations of the wearing conditions parameters values with respect to the reference position of the eyewear equipment. This tolerance defines maximal tolerable wearing condition parameters. The maximal tolerable wearing condition parameters define the threshold value relative to one wearer's wearing condition parameter. The tolerable variation is considered according to a level of discomfort caused to the wearer. The threshold value corresponds to the maximal level of discomfort tolerated by the wearer. The level of discomfort is indicative of an index of visual performance of the wearer wearing the eyewear equipment in the current position. If the variation between the current position and the reference position is above the predetermined threshold for at least one wearing condition parameter, the frequency of the evaluations is increased.

Advantageously, the method enables to determine in a quick manner if the eyewear equipment provided to the wearer is suitable and correctly fitted. Additionally, this method does not request the wearer to go to an optician practitioner to determine whether the new eyewear equipment is adapted and correctly fitted.

Another advantage of a recurrent position evaluation is an early detection of the fact that the eyewear equipment is no longer adapted to the wearer or correctly fitted. This detection may be detected if to variation of the position of the eyewear equipment with respect to the reference position is above a predetermined threshold value relative to at least one wearer's wearing condition parameter. The predetermined threshold may comprise the eye-lens distance, the pantoscopic angle and other data related to the wearer's wearing conditions parameters values. The wearer may tolerate variations of the wearing conditions parameters values with respect to the reference position of the eyewear equipment. This tolerance defines maximal tolerable wearing condition parameters. The maximal tolerable wearing condition parameters define the threshold value relative to one wearer's wearing condition parameter. The tolerable variation is considered according to a level of discomfort caused to the wearer. The threshold value corresponds to the maximal level of discomfort tolerated by the wearer. The level of discomfort is indicative of an index of visual performance of the wearer wearing the eyewear equipment in the current position. If the variation between the current position and the reference position is above the predetermined threshold for at least one wearing condition parameter, the frequency of the evaluations is increased.

If the level of discomfort caused by a variation of at least one wearing parameter variation remains above a given threshold, the wearer and/or the optician may be informed that the eyewear equipment needs to be modified such as screws of the eyewear equipment frame needing to be tighten or a need of a new eyewear equipment frame. These modifications of the frame aim at providing an eyewear equipment adapted to the wearer and correctly fitted on the wearer's head. Instead of eyewear equipment modification, the wearer and/or the optician may be informed that a new eyewear equipment should be provided to the wearer.

The method for determining a position variation of an eyewear equipment worn by a wearer may further comprise a step S8 of obtaining a threshold value.

The threshold value is a limit value associated with a level of discomfort of the wearer wearing the eyewear equipment. In other words, the threshold value represent a value of position variation of the eyewear equipment for which the level of discomfort caused to the wearer is considered to be to important. The level of discomfort is indicative of an index of visual performance of the wearer wearing the eyewear equipment in the current position.

According to an embodiment of the disclosure, the index of visual performance relates to a resulting astigmatism.

The term 'astigmatism' is a well-known term used to denote the data pair formed by an amplitude value and a value of angle. Although this is an abuse of language, it is also sometimes used to denote the amplitude of the astigmatism only. The context allows those skilled in the art to understand which usage of the term is intended. The resulting astigmatism, referred as ASR, is the difference between the prescribed astigmatism (wearer astigmatism) and the lens-generated astigmatism.

According to an embodiment of the disclosure, the index of visual performance relates to an acuity loss.

The acuity loss, referred as ACU_P, is defined as a function of the relative acuity at a given point of the object space ($\alpha$, $\beta$, ProxO), according to following equation:

$$ACU\_P(\alpha,\beta,ProxO) = -\log(AC\%\_P(\alpha,\beta,ProxO)/100)$$

where "log" is the logarithm in base 10.

The relative acuity, referred as AC %_P, is defined as the result of a function of the mean refractive power error, PE_P, and of the resulting astigmatism, ASR, according to an acuity model, at a given point of the object space ($\alpha$, $\beta$, ProxO).

The mean refractive power error, referred as PE_P, is defined as the mean refractive power difference between the actual addition brought by the lens and the proximity, at a given point of the object space ($\alpha$,$\beta$,ProxO), according to following equation:

$$PE\_P(\alpha,\beta,ProxO) = PPO(\alpha,\beta,ProxO) - (PPO(FV) - ProxFVp) - ProxO$$

where PPO(FV) is the mean refractive power of the prescription of the wearer according to the far-vision gaze direction, for an object located at a distance corresponding to ProxFVp.

According to an embodiment of the disclosure, the index of visual performance relates to accommodation effort.

The accommodation effort may be defined by the amplitude of accommodation of a person, i.e. the difference in dioptric power between the eye at rest and the fully accommodated eye. Usually, the amplitude of accommodation is measured by the method of spheres in which the person is asked to look at an object placed at a specific distance while different lenses with gradually varying optical powers are used to change his accommodation.

According to an embodiment of the disclosure, the index of visual performance relates to vergence effort.

According to an embodiment of the disclosure, the index of visual performance relates to diplopia.

According to an embodiment of the disclosure, the method for determining a position variation of an eyewear equipment worn by a wearer may comprise a step S0 of obtaining lens data.

The lens data relates to a prescription of the wearer. The term "prescription" is to be understood to mean a set of optical characteristics of optical power, of astigmatism, of prismatic deviation, determined by an ophthalmologist or optometrist in order to correct the vision defects of the eye, for example by means of a lens positioned in front of his eye. For example, the prescription for a myopic eye comprises the values of optical power and of astigmatism with an axis for the distance vision.

The lens data may further relate to a design of at least one lens of the eyewear equipment. The term "design" is a widely used wording known from the man skilled in the art to designate the set of parameters allowing to define an optical function of a generic optical system; each ophthalmic lens manufacturer has its own designs, particularly for aspherical lens and for progressive lens.

According to an embodiment of the disclosure, the threshold value of the wearer may be determined based at least on the lens data and the position variation of the eyewear equipment. Based on the lens data one may easily compute the values of the index of visual performance for each specific position of the eyewear equipment on the face of the wearer, for example in the form of a resulting astigmatism map represented in FIG. 4. From such relation, the variation of the index of performance may be expressed as a function of the position variation of the eyewear equipment and the threshold value may be defined as a value of position variation for which the index of visual performance, and thus the level of discomfort, drop from a specific amount.

According to an embodiment of the disclosure, the method for determining a position variation of an eyewear equipment worn by a wearer may further comprise a step S2 of obtaining sensitivity data.

The sensitivity data relates to the sensitivity of the wearer to optical aberrations. The sensitivity data may relate to blur tolerance and/or fusional reserve and/or sensitivity to astigmatism. The sensitivity of the wearer to optical aberrations can be determined objectively, for example thanks to a perception test, or subjectively by means of an image quality gradation test. This sensitivity to optical aberration can be manifested among others as discomfort (pitch) and/or a change of the perception of visual index (for example: curvatures), and/or motor skills (for example: modification of eye-head coordination, postural oscillation) and/or sensorimotor loops (for example: change in response times). WO 2019/206905 A1 explains in details how the sensitivity of the wearer is determined.

The sensitivity of the wearer may further be used in association with the lens data and the position variation to determine the threshold value. More precisely, the sensitivity data are used to ponder the threshold value. Indeed, a wearer having a high tolerance to optical aberration will be less impacted and feel less discomfort when the position of the eyewear equipment varies. On the contrary, a wearer having a high sensitivity and thus a low tolerance to optical aberration will feel more discomfort for a small variation of position of the eyewear equipment.

The method for determining a position variation of an eyewear equipment worn by a wearer may further comprise a step S16 of comparing the threshold value associated with a level of discomfort and the position variation of the eyewear equipment.

The method is illustrated with an example in which the index of visual performance corresponds to the resulting astigmatism. However, it appears clearly and unambiguously to the person skilled in the art that the threshold value may be determined for any of the above mentioned index of visual performance.

Figure 4A:
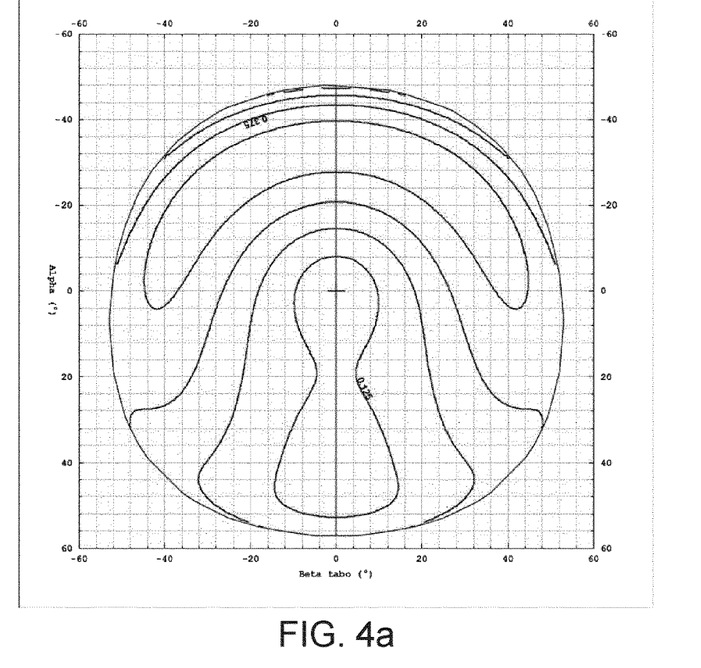
FIGS. 4a and 4b illustrate resulting astigmatism maps of a wearer wearing a first eyewear equipment.
Figure 4B:
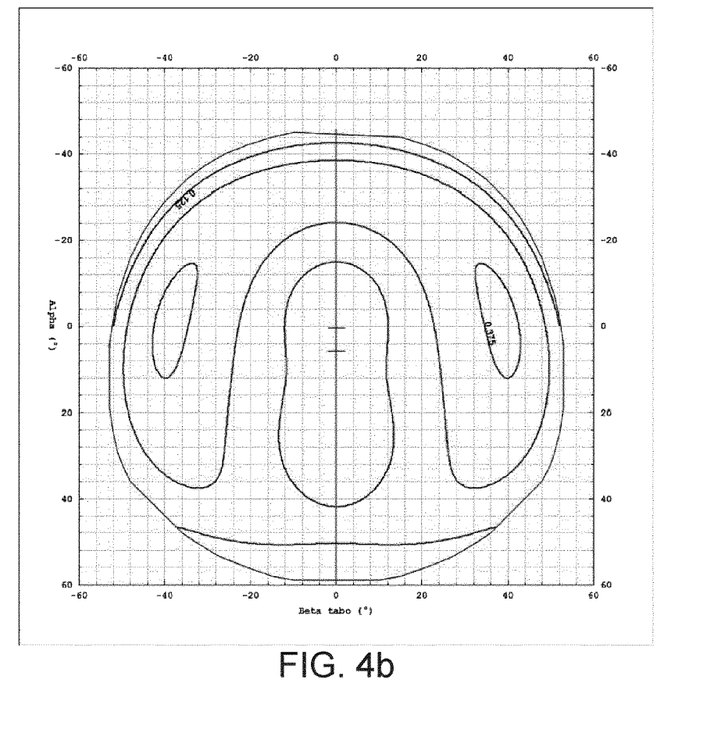

FIG. 4 illustrates resulting astigmatism maps of a lens of the eyewear equipment worn by the wearer. In this example, the lens is a single vision lens with the following prescription: Sph=−4 D; Cyl=0; Axis=0 deg. For such lens, the wearer will experience a loss in visual performance if the resulting astigmatism exceeds 0.12 D. The cross at (Alpha=0, Beta=0) corresponds to the fitting cross of the lens. In FIG. 4a, the lens is positioned on the face of the wearer in the reference position. At the fitting cross, the resulting astigmatism ASR for a straight gaze is 0.00 D. In FIG. 4b, the lens is positioned on the face of the wearer with a position variation (x,y) of 2.5 mm with respect to the reference position. For a straight gaze, the resulting astigmatism ASR is below 0.04 D. Considering that a difference of resulting astigmatism ASR below 0.12 D will not affect the visual performance of the wearer, the threshold value can be set as high as 7 mm for the present lens.

Figure 5A:
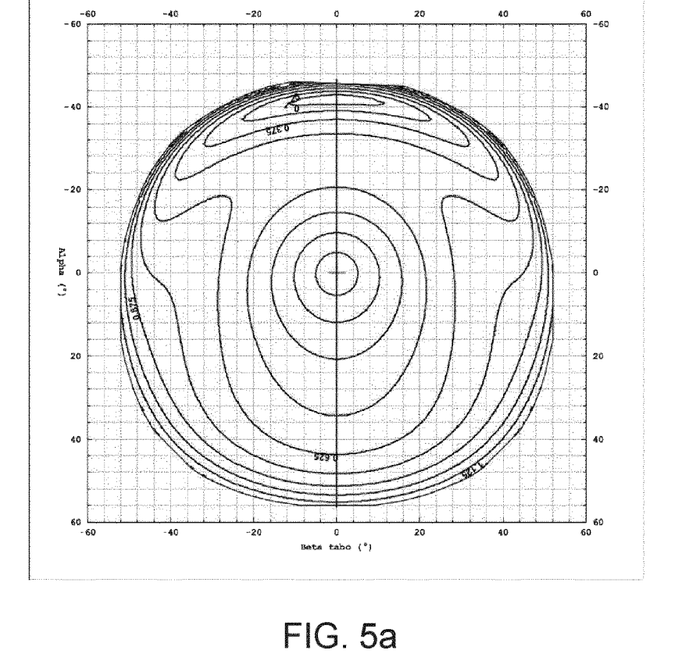
FIGS. 5a and 5b illustrate resulting astigmatism maps of a wearer wearing a second eyewear equipment.
Figure 5B:
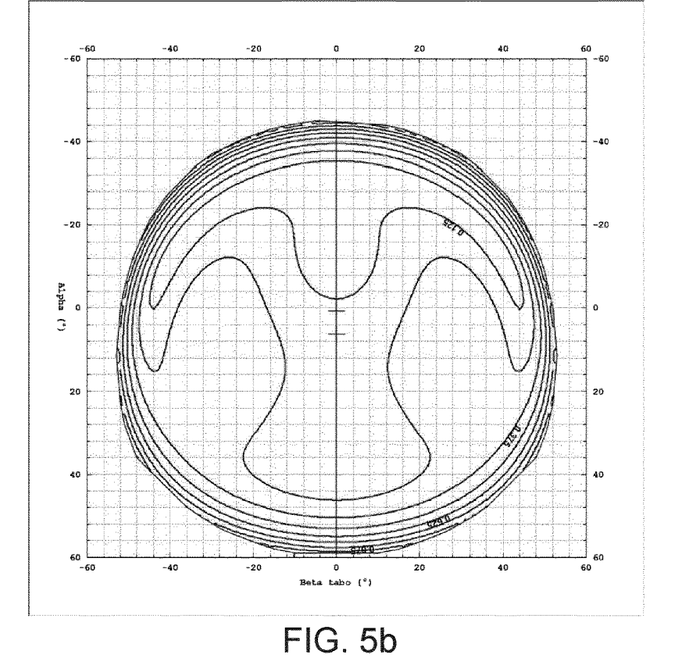

FIG. 5 illustrates resulting astigmatism maps of another lens of the eyewear equipment worn by the wearer. In this example, the lens is a single vision lens with the following prescription: Sph=−10 D; Cyl=0; Axis=0 deg. For such lens, the wearer will experience a loss in visual performance if the resulting astigmatism exceeds 0.12 D. The cross at (Alpha=0, Beta=0) corresponds to the fitting cross of the lens. In FIG. 5a, the lens is positioned on the face of the wearer in the reference position. At the fitting cross, the resulting astigmatism ASR for a straight gaze is 0.00 D. In FIG. 5b, the lens is positioned on the face of the wearer with a position variation (x,y) of 2.5 mm with respect to the reference position. For a straight gaze, the resulting astigmatism ASR is 0.15 D. Considering that a difference of resulting astigmatism ASR above 0.12 D will affect the visual performance of the wearer, the threshold value should be set below 2.5 mm for the present lens.

In another example, two wearers are wearing the same eyewear equipment comprising a lens with the following prescription: Sph=−6 D; Cyl=0; Axis=0 deg. The first wearer is sensitive to an astigmatism error of 0.12 D while the second wearer is sensitive to an astigmatism error of 0.06 D. The resulting astigmatism for a gaze direction at (0,0) is equal to 0.06 D for a vertical shift of the eyewear equipment equal to 2.5 mm, and equal to 0.12 D for a vertical shift of the eyewear equipment equal to 5 mm. The first wearer will experience a significant decrease of visual performance for position variation of the eyewear equipment higher than 2.5 mm. Therefore, for the first wearer, the threshold value will be set at 2.5 mm. The second wearer will experience a significant decrease of visual performance for position variation of the eyewear equipment higher than 5 mm. Therefore, for the second wearer, the threshold value will be set at 5 mm.

According to an embodiment of the disclosure, during step S18, a notification is sent if the position variation is higher than or equal to the threshold value. For example, a notification is sent to the wearer. In case the wearer of the eyewear equipment is a child, the notification may be sent to a different person, for example one of its parent. Similarly, the notification may be sent to the eye care professional to indicate that the eyewear equipment may need to be re-adapted to the wearer or changed. Advantageously, alerting the wearer and/or the eye care professional that the eyewear equipment may no longer be adapted to the wearer allows both parts to easily and rapidly take action to correct or change the eyewear equipment.

Figure 6:
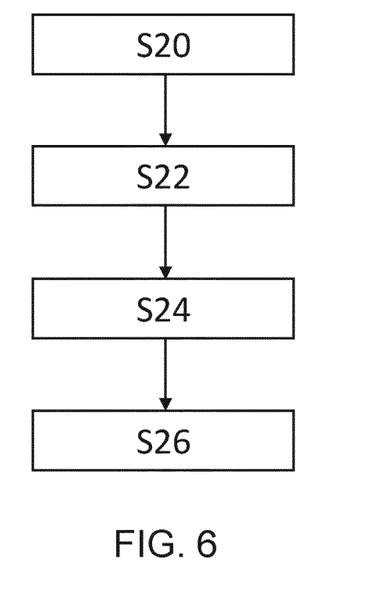
FIG. 6 illustrates a chart-flow embodiment of the method for selecting a most adapted eyewear equipment for a wearer.

With reference to FIG. 6, the disclosure further relates to a method, for example implemented by computer means, for selecting the most adapted optical equipment for a wearer.

The method for selecting the most adapted optical equipment for a wearer comprises a step S20 of providing multiple eyewear equipment. For example, at least two eyewear equipment are obtained. In the sense of the disclosure, the term "obtaining" may refer to either one of "providing", "selecting", or "determining".

The method for selecting the most adapted optical equipment for a wearer comprises a step S22 of determining a position variation of the eyewear equipment worn by the wearer for each of the provided eyewear equipment according to the method of the disclosure.

During step S24, the position variations determined for each of the obtained eyewear equipment are compared between each other.

The method for selecting the most adapted optical equipment for a wearer comprises a step S26 of selecting the most adapted eyewear equipment for the wearer. The most adapted eyewear equipment for the wearer is the eyewear equipment for which the position variation is the smallest.

Figure 7:
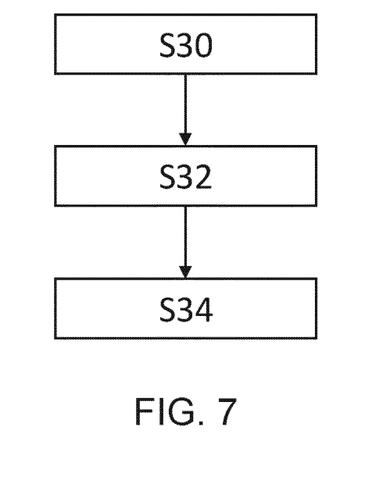
FIG. 7 illustrates a chart-flow embodiment of the method for adjusting an optical function of an electro-active eyewear equipment worn by a wearer.

With reference to FIG. 7, the disclosure further relates to a method, for example implemented by computer means, for adjusting an optical function of an electro-active eyewear equipment worn by a wearer. The electro-active eyewear equipment comprises a frame and at least one programmable lens having an electro-active optical function. The electro-active optical function of the programmable lens can be controlled by an optical function controller. The optical function may correspond to a function providing for each gaze direction the effect of the optical lens on the light ray passing through the optical lens. The optical function may comprise a dioptric function, light absorption, polarizing capability, reinforcement of contrast capacity, etc.

During step S30, a position variation of the electro-active eyewear equipment is determined according to the method of the disclosure.

The method for adjusting an optical function of an electro-active eyewear equipment worn by a wearer further comprise a step S32 of obtaining prescription data indicative of a prescription of the wearer.

The method for adjusting an optical function of an electro-active eyewear equipment worn by a wearer further comprise a step S34 of adjusting the optical function of the electro-active eyewear equipment based on the position data and the prescription data.

According to a further aspect, the disclosure relates to a computer program product comprising one or more stored sequences of instructions that are accessible to a processor and which, when executed by the processor, causes the processor to carry out the steps of a method according to the disclosure.

The disclosure further relates to a computer readable medium carrying one or more sequences of instructions of the computer program product according to the disclosure. Furthermore, the disclosure relates to a program which makes a computer execute a method of the disclosure.

The disclosure also relates to a computer-readable storage medium having a program recorded thereon; where the program makes the computer execute a method of the disclosure.

The disclosure further relates to a device comprising a processor adapted to store one or more sequence of instructions and to carry out at least one of the steps of a method according to the disclosure.

The disclosure further relates to a non-transitory program storage device, readable by a computer, tangibly embodying a program of instructions executable by the computer to perform a method of the present disclosure.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMS) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Many further modifications and variations will be apparent to those skilled in the art upon making reference to the foregoing illustrative embodiments, which are given by way of example only and which are not intended to limit the scope of the disclosure, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the disclosure.

The invention claimed is:

1. A method for determining a position variation of an eyewear equipment worn by a wearer, the method comprising:

obtaining reference data representing a reference position of an eyewear equipment worn by the wearer, the eyewear equipment comprising at least one ophthalmic lens and a frame on which the at least one ophthalmic lens is mounted;

determining at least one reference position parameter indicative of a reference position of the eyewear equipment on the face of the wearer based on the reference data;

obtaining current data representing a current position of the eyewear equipment worn by the wearer;

determining at least one current position parameter indicative of a current position of the eyewear equipment in front of the eyes of the wearer based on the current data;

comparing the reference and current positions parameters to determine a position variation of the eyewear equipment worn by the wearer;

obtaining a threshold value associated with a level of discomfort of the wearer that is indicative of an index of visual performance of the wearer wearing the eyewear equipment in the current position;

comparing the threshold value and the position variation of the eyewear equipment worn by the wearer; and sending a notification to the wearer when the position variation of the eyewear equipment worn by the wearer is higher than the threshold value.

2. The method according to claim 1, wherein the obtaining the current data, the determining the current position parameter, and the comparing the reference and current position parameters are repeated over time to evaluate the position variations of the eyewear equipment over time.

3. The method according to claim 1, wherein the index of visual performance relates to one or more of:
   (i) an acuity loss,
   (ii) an accommodation effort,
   (iii) a resulting astigmatism,
   (iv) a vergence effort, and
   (v) a diplopia.

4. The method according to claim 1, further comprising:
   obtaining lens data relating at least to a prescription of the wearer and/or the design of the at least one lens of the eyewear equipment; and
   determining a threshold value corresponding to a level of discomfort of the wearer based on the lens data and the position variation of the eyewear equipment.

5. The method according to claim 1, further comprising obtaining sensitivity data indicative of the sensitivity of the wearer to optical aberrations, and
   wherein the threshold is determined based on the lens data, the position variation of the eyewear equipment, and the sensitivity data.

6. The method according to claim 1, wherein the position of the eyewear equipment corresponds to the position of the two lenses of the eyewear equipment worn by the wearer in front of each respective eye of the wearer.

7. The method according to claim 1, wherein the reference and current data comprises at least one picture of the face of the wearer wearing the eyewear equipment.

8. The method according to claim 1, wherein the reference and current data comprises a three-dimensional scan of the face of the wearer wearing the eyewear equipment.

9. The method according to claim 1, wherein the reference and current position parameter corresponds to one or more of:
   (i) a pupil position in a boxing reference frame for a primary gaze posture, (ii) a position of at least one eyewear equipment feature relative to at least one face feature,
(iii) a vertex distance,
(iv) a pantoscopic angle of the lens according to the wearer primary gaze posture,
(v) a wrap angle of the lens,
(vi) a lens rotation angle, and
(vii) a pupil position relative to the lens fitting cross.

10. The method according to claim 1, wherein the current data are obtained after at least a minimal wearing time.

11. The method according to claim 1, wherein the minimal wearing time is two weeks.

12. A method for selecting eyewear equipment for a wearer, the method comprising:
    providing a plurality of eyewear equipment;
    determining the position variation of the eyewear equipment worn by the wearer for each eyewear equipment according to the method of claim 1;
    comparing the position variation of each eyewear equipment; and
    selecting the eyewear equipment having the smallest position variation.

13. A method for adjusting an optical function of an active lens of an electro-active eyewear equipment worn by a wearer, the method comprising:
    determining a position variation of the electro-active equipment according to the method of claim 1;
    obtaining prescription data indicative of a prescription of the wearer; and
    adjusting the optical function of the active lens based on the position variation and the prescription data.

14. A computer program product embodied on a non-transitory data storage medium, the computer program product comprising one or more stored sequences of instructions that are accessible to a process and which when executed by the processor, cause the processor to carry out the method of claim 1.

* * * * *